United States Patent
Auzerais et al.

[11] Patent Number: 5,790,185
[45] Date of Patent: Aug. 4, 1998

[54] VIDEO INSPECTION OR LOGGING TOOL

[76] Inventors: François Auzerais, 120-12 Prospect, Ridgefield, Conn. 06877; Robert J. Schroeder, 71 Castle Hill Rd., Newtown, Conn. 06470; Benoît Couët, 11 Kellogg St., Bethel; Jeffrey A. Tarvin, 18 Fawn Ridge, Brookfield, both of Conn. 06804

[21] Appl. No.: 759,691

[22] Filed: Dec. 6, 1996

[51] Int. Cl.$^6$ .................................................. H04N 7/18
[52] U.S. Cl. .................................. 348/84; 348/85; 348/131
[58] Field of Search ................................. 348/82, 84, 85, 348/131, 335, 369, 370; H04N 7/18

[56] References Cited

U.S. PATENT DOCUMENTS

| | | | |
|---|---|---|---|
| 3,041,393 | 6/1962 | Hennig | 348/82 |
| 3,761,623 | 9/1973 | Hara | 348/84 |
| 3,958,080 | 5/1976 | Schadler | 348/84 |
| 4,855,820 | 8/1989 | Barbour . | |
| 4,977,418 | 12/1990 | Canty | 348/82 |
| 5,134,471 | 7/1992 | Gendron et al. . | |
| 5,140,319 | 8/1992 | Riordan . | |
| 5,355,128 | 10/1994 | Riordan . | |
| 5,402,165 | 3/1995 | Linville et al. . | |
| 5,543,972 | 8/1996 | Kamewada . | |

FOREIGN PATENT DOCUMENTS

| | | | |
|---|---|---|---|
| 0 264 511 | 4/1988 | European Pat. Off. | H04N 7/18 |

OTHER PUBLICATIONS

Shapiro, Jerome M., Embedded Image Coding Using Zerotrees of Wavelet Coefficients, *IEEE Transactions on Signal Processing*, vol. 41, No. 12, (Dec. 1993) pp. 3445-3462.

Said, Amir and Pearlman, William A., A New, Fast, and Efficient Image Codec Based on Set Partitioning in Hierarchical Trees, *IEEE Transactions on Circuits and Systems for Video Technology*, vol. 6, No. 3 (Jun. 1996) pp. 244-250.

Schlumberger Wireline & Testing brochure on Pipeline Inspection Services, SMP-5154 Apr. 1992.

Steven D. Moore, Video Logging: Your Downhole Eye, Petroleum Engineer International (Oct. 1991).

Hitwell Ad See What You're Missing.

Hitwell Ads on Camera Models HTP-BW-01, HR-C-01, and HL-BW-01.

Halliburton Ads on HawkEye Video System and Fiber Optic Video System.

*Primary Examiner*—Howard W. Britton
*Attorney, Agent, or Firm*—Keith G. W. Smith

[57] ABSTRACT

A video logging tool is described which is particularly well adapted for production logging of oil or gas wells. The tool has both an end view optical system and a side view optical system for imaging side and end view on a CCD array in a camera.

28 Claims, 9 Drawing Sheets

VIDEO INSPECTION OR LOGGING TOOL

BACKGROUND OF THE INVENTION

This invention relates to a video inspection or logging tool, for logging boreholes or inspecting the inside of pipelines to locate corrosion.

Video logging tools are used for inspecting the side wall of a borehole or for inspecting the casing if the borehole is cased. They are also used for looking downward into the borehole. They can view the formation fluids being produced by an oil or gas well. These formation fluids are usually some combination of oil, gas and water. If dark oil is being produced alone, these video logging tools are not very effective because the oil is essentially opaque over the distances required for useful viewing. However if oil is being produced alone, the well is probably in good shape and there is not much need for viewing.

The more interesting case is when oil and water are being produced together. In that case, such tools can show the oil bubbles flowing up through the water. The water provides enough transparency so that the column of produced fluids or the side wall of the borehole or the casing can be viewed. Likewise, perforations in the casing through which the formation fluids are being produced can also be seen.

Video logging tools are known. One such tool provides an end view looking axially down the borehole into the column of formation fluids being produced. The end view has a field of view sufficiently large to include a portion of the borehole or casing wall surrounding the column of formation fluids. However the axial length of the portion of the wall which can be viewed is somewhat limited.

Video logging tools are also known which provide a side view directed at the borehole wall. Such tools give a better image of the borehole or casing wall, including perforations, but they lack the end view of the borehole fluids which are being produced up the well.

Known video logging tools use an incandescent lamp, typically a halogen lamp, to light the end view or the side view as the case may be. Such lamps turn on relatively slowly because the incandescent filament has to heat up and cool down. Furthermore they require considerable power, which is a disadvantage in a downhole tool.

It is an object of the present invention to provide a video logging tool having an improved optical arrangement over the tools of the prior art.

It is also an object of the present invention to provide such a tool with an improved lighting system.

Finally it is an object of the invention to provide a video logging tool having both end and side viewing arrangements.

SUMMARY OF THE INVENTION

In accordance with one aspect of the invention, the video logging tool comprises a video camera mounted in a housing sized to be lowered into and raised out of a borehole. The tool includes both an end viewing optical system and a side viewing optical system, and means for lighting both the end viewing zone and the side viewing zone. Preferably the lighting means comprises a plurality of light emitting diodes (LEDs). The end view and the side view are imaged on to the same image plane in the camera, and a charge coupled device (CCD) array is located in the image plane. The end view and the side views can be taken simultaneously.

In accordance with another aspect of the invention there is no end viewing optical system, but the side viewing optical system is arranged in a particular way. Specifically, the side viewing optical system comprises a block, preferably made of sapphire or silica with an outer coating of sapphire. The block has an internal concave surface coated with a mirror, which reflects the side view toward the camera. A camera lens group focuses the side view onto a CCD array in the image plane of the camera.

In another embodiment of the invention, the side viewing optical system comprises two or three fish-eye lenses, and a prism for transmitting the two or three side images separately to the camera.

In the present specification, the term "video" is not intended to imply any particular video format, such as composite video used in NTSC or other formats.

DESCRIPTION OF THE PREFERRED EMBODIMENTS

Figure 1:
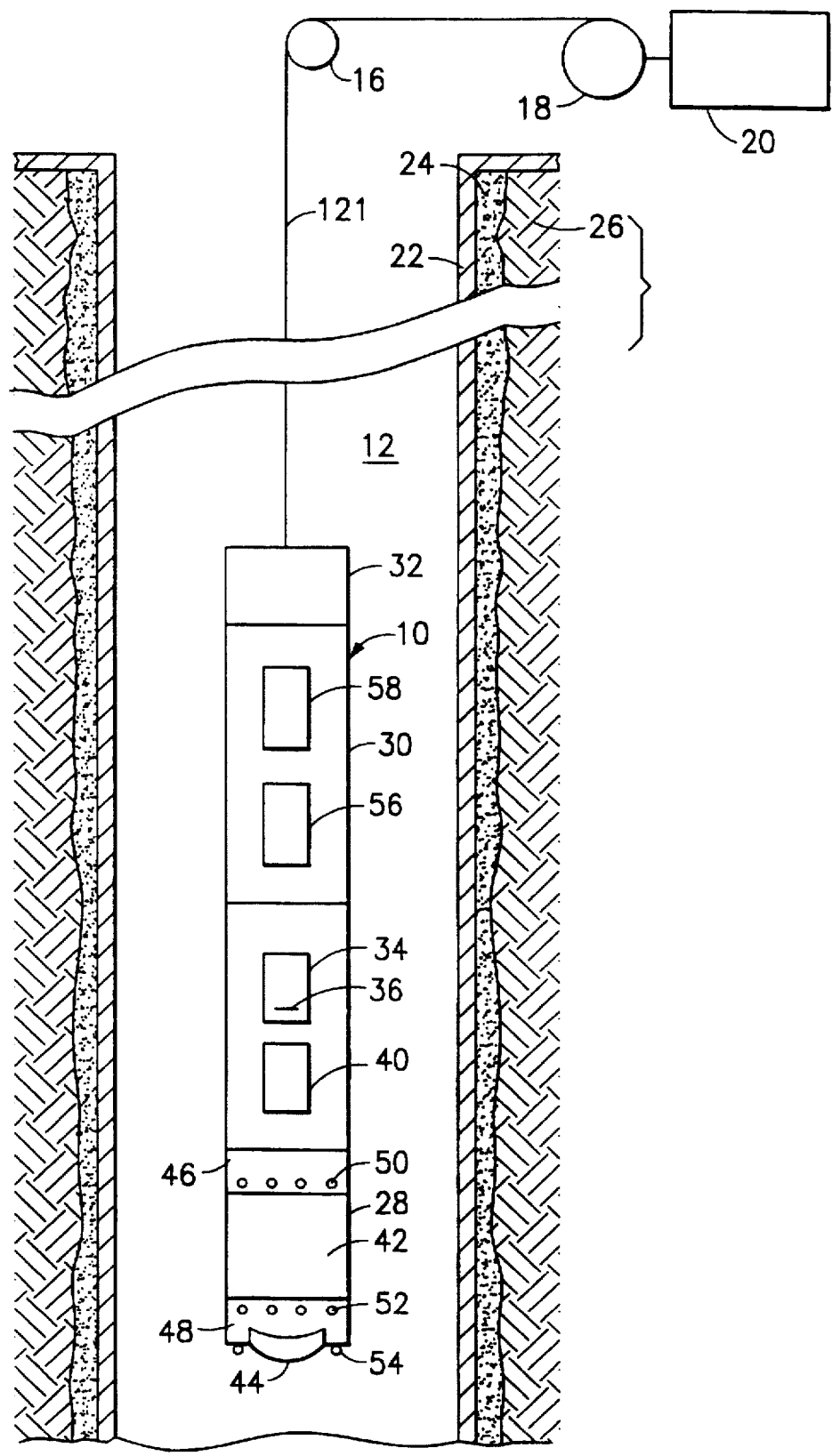
FIG. 1 is a schematic diagram of a video logging tool in accordance with the invention, disposed in a borehole.

Turning now to the drawings, FIG. 1 shows a video borehole logging tool 10, in accordance with the invention, suspended in a borehole 12 by a cable 14. The cable passes over a sheave 16 at the earth's surface and is spooled on a drum 18 by which the tool is lowered into the borehole 12 and raised out of it. The drum 18 is connected to surface instrumentation 20 which controls the operation of the drum and of the tool 10. The surface instrumentation 20 also provides power to the tool.

The borehole 12 is an oil or gas well and has a casing 22 cemented at 24 to the earth formation 26. The tool 10 comprises a lower optical module 28 (which will be described in connection with FIG. 2), a control module 30 and a telemetry module 32 for transmitting the video images to the surface for further processing in the surface instrumentation 20 and subsequent displaying.

The optical module 28 comprises a CCD camera 34 having a CCD array 36 in what will become the image plane. Disposed in front of the camera 34 is an optical group 40 which comprises an objective for the camera. An optical block 42 is disposed below the objective group 40 and forms part of a side viewing optical system and pressure resistant window. An end viewing optical system 44 is disposed below the optical block 42 and forms a pressure resistant window. The optical block 42 is secured between flanges 46 and 48 in each of which is disposed a plurality of light emitting diodes (LEDs) 50 and 52 respectively, arranged circumferentially around the flanges. The LEDs 50 and 52 comprise a side lighting system for lighting the side zone as far as the casing 22 in the vicinity of the side viewing optical block 42.

Another ring of LEDs 54 is located on the end face of the lower flange 48 and surrounds the end viewing optical system 44. The LEDs 54 comprise an end lighting system for lighting the end zone below the end viewing optics 44.

The control module 30 comprises a power supply and driver 56 for the camera 34 and the LEDs 50, 52, and 54. The control module also comprises signal conditioning means 58 for taking the output signal from the camera 34, digitizing and processing the camera output signal and compressing it for transmission to the surface by the telemetering module 32.

Figure 2:
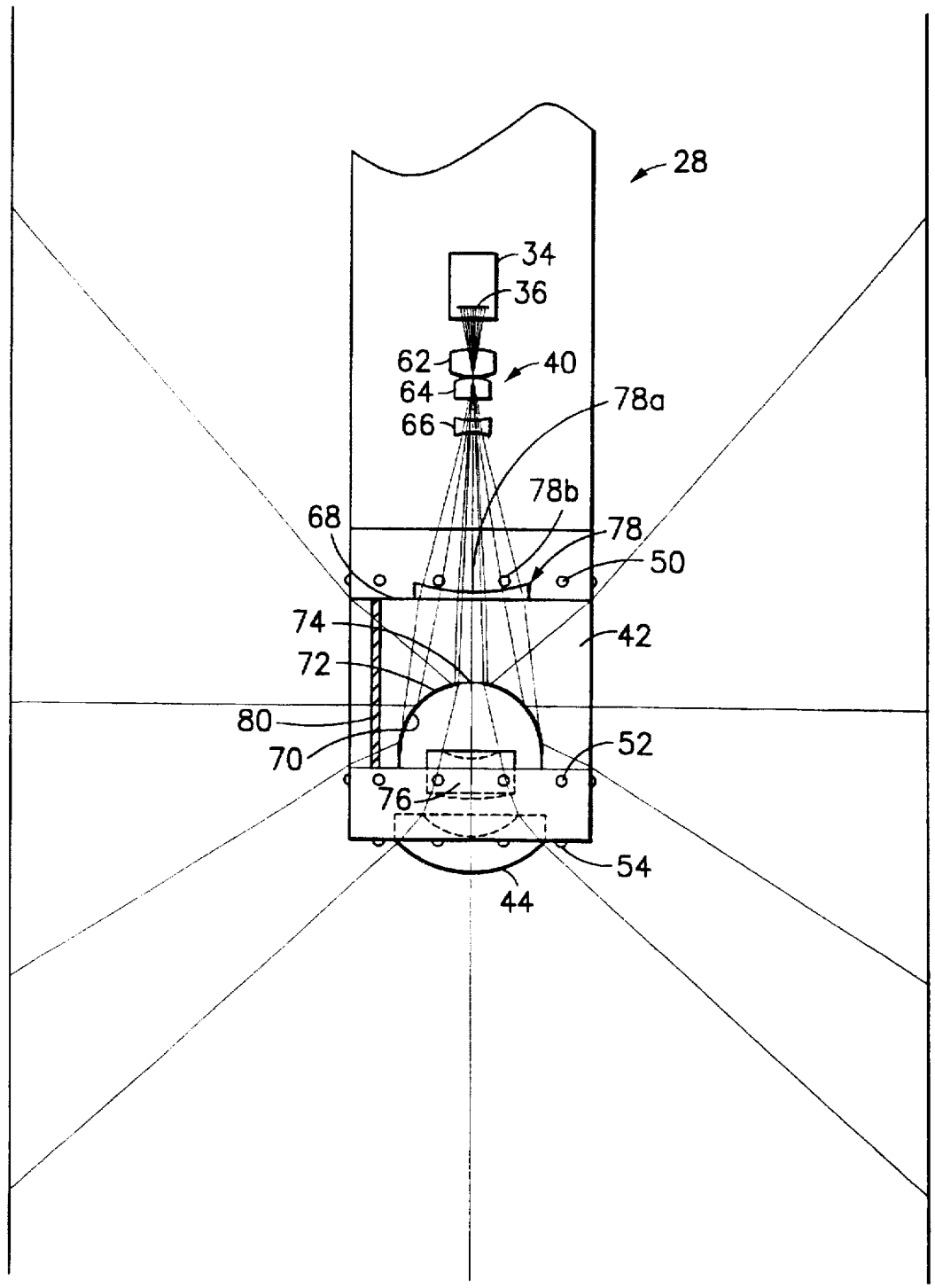
FIG. 2 is a schematic view, partly in cross section, of the optical module of the tool of FIG. 1.

FIG. 2 shows the optical systems of the optical module 28 in more detail. The camera lens group 40 comprises a doublet 62, a plano-convex lens 64 and a bi-concave lens 66. The optical block 42, which forms part of both the side viewing system and the end viewing system, comprises a planar upper surface 68 and a hemispherical concave lower surface 70. The concave surface 70 is coated at 72 with a mirror made of aluminum, silver or a dielectric coating chosen for the illumination wave-lengths of the LEDs 50, 52 and 54. A central aperture 74 is not coated with the mirror, so as to allow the end viewing light rays to pass through. The end viewing optical system includes the end window 44 which is formed by a concave convex meniscus lens. A second concave convex meniscus lens 76 also forms part of the endviewing optical system, as well as the concave surface of the block 42 at the aperture 74. Finally, a bi-focal correcting lens 78 is disposed on the upper planar surface of the optical block 42. This lens has an inner portion 78a through which the end viewing light rays pass, and a peripheral portion 78b through which the side viewing light rays pass.

The optical block 42 is held in place by three struts 80, only one of which is shown in cross section in FIG. 2, connected between the flanges 46 and 48.

The LEDs, 50, 52, and 54 preferably emit light in the near infrared having a predominant wavelength of 880 nanometers in the example described. The near infrared penetrates through oil better than visible light does. This is explained in co-pending application Ser. No. 08/483,137 by Auzerais and Schroeder, assigned to the same assignee as the present application. Furthermore, LEDs turn on and off quickly and so can be operated with a relatively low duty cycle thereby reducing the power consumption. They also enable stop action photography.

The optical systems described above have been designed and optimized for use with 880 nanometer light in borehole fluids such as oil and water, using a commercial software package called Code V marketed by Optical Research Associates of Pasedena, Calif. The field of view of the side view in oil and water extends from approximately plus 45 degrees to minus 45 degrees. In an oil or gas well cased with a casing 6 inches in diameter, this would provide a side view of the casing approximately 6 inches in height and extending circumferentially around the entire casing.

The end viewing optical system provides a conical field of view in oil and water of approximately plus or minus 35 degrees. The size of the aperture 74 is chosen to achieve the desired field of view for the side view. The end view optics obtain the desired view field of view for the given aperture.

The optical systems described above provide a depth of view for the side view approximately from the outer side surface of the optical block 42 to the wall of a 6 inch casing. The depth of view for the end view is approximately from the end window 44 to nearly infinity.

The optical block 42 and the end window 44 must be pressure resistant and be able to withstand abrasion. Preferably they are made of sapphire, or alternatively, of fused silica having a sapphire coating on their exterior surfaces.

Figure 3:
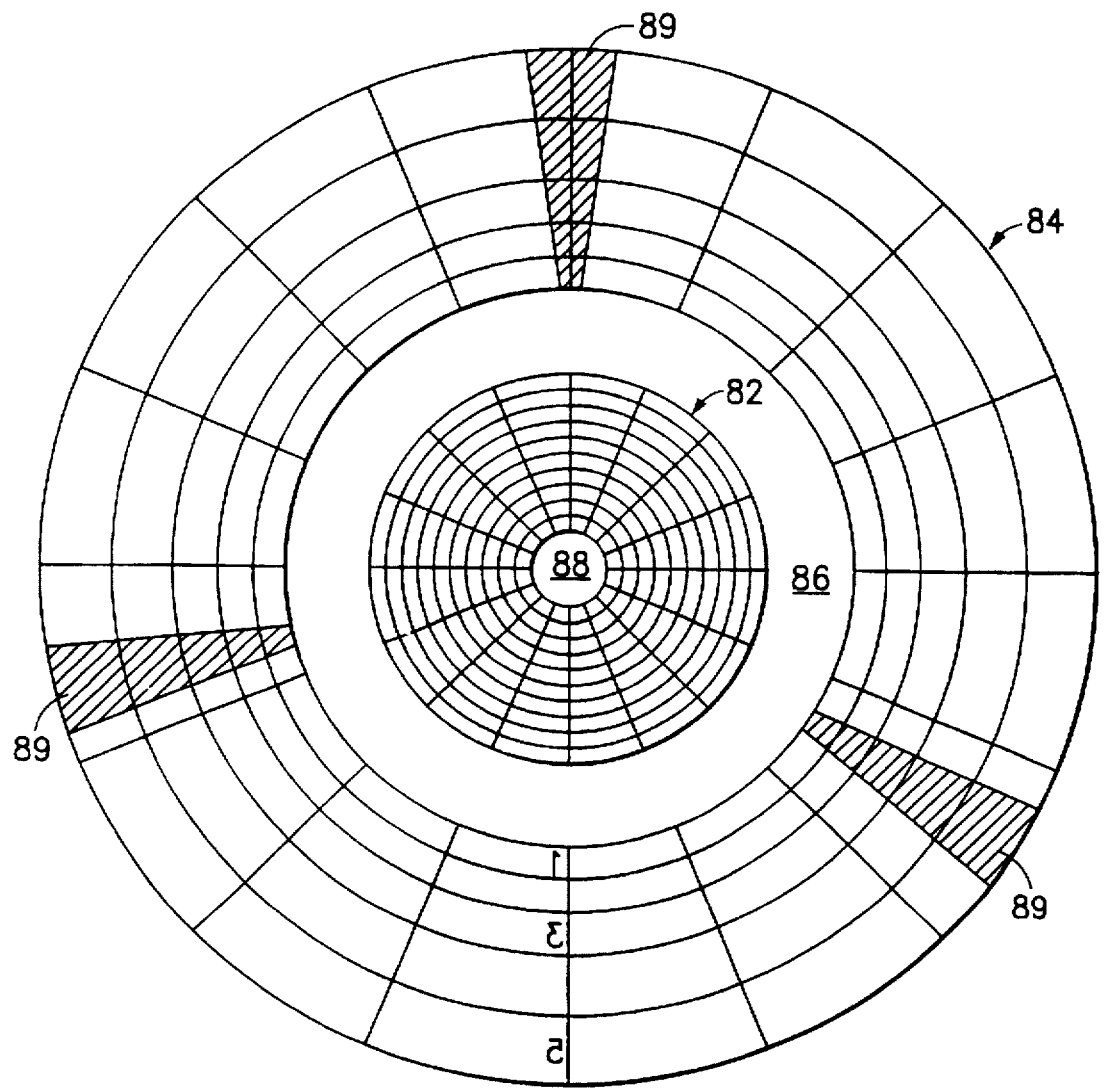
FIG. 3 shows the combined end and side views provided by the tool of FIG. 1, before the distortion in the side view has been corrected.

The optical systems are arranged to image both the side view and the end view onto the same plane, which is the plane of the CCD array 36. The image seen by the CCD 36 is shown in FIG. 3. This represents a 6 inch pipe, simulating a 6 inch casing, which has been graduated with circumferential lines one inch apart, and 16 vertical or axial lines equally spaced around the circumference. The image shows the end view 82, the side view 84 and the "dead zone" 86 between the end and side views. The central circle 88 is the end of the pipe. The obstructions caused by the struts 80 are shown at 88 in FIG. 3.

The side view 84, which is reflected off the mirror 72, is reversed left for right as shown by the three numerals 1, 3, and 5 in the figure. The side view is also distorted in the vertical or axial direction of the pipe, because of the curvature of the hemispherical mirror 72.

Figure 4:
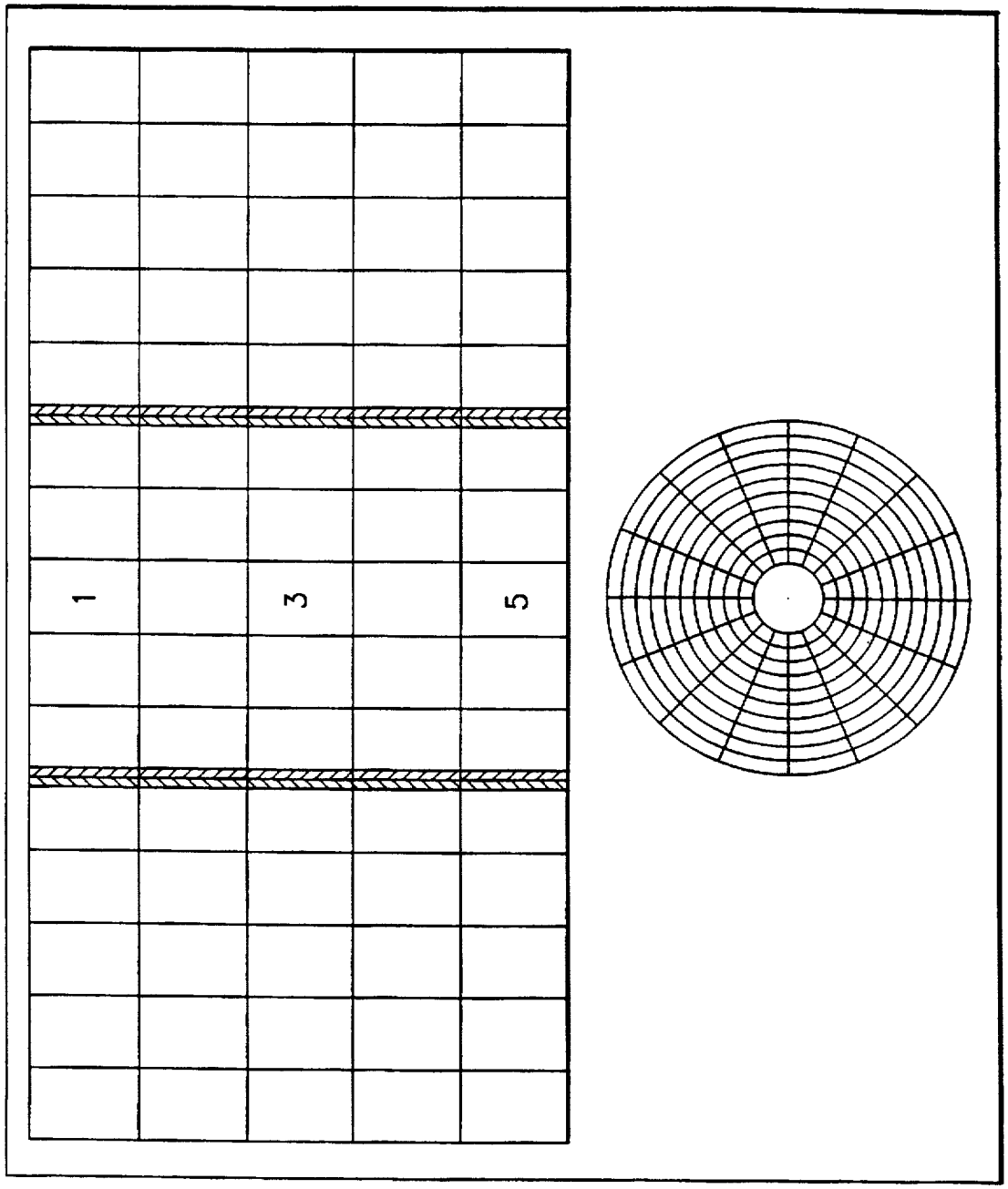
FIG. 4 shows the end and side views after the side view has been converted to rectilinear coordinates to remove the distortion.

FIG. 4 shows the image of FIG. 3 after it has been transmitted to the surface and processed in the surface instrumentation 20 to convert the side view to rectilinear coordinates, thereby removing the distortion. The same software package, Code V, can be used to define this rectilinear conversion.

Figure 5:
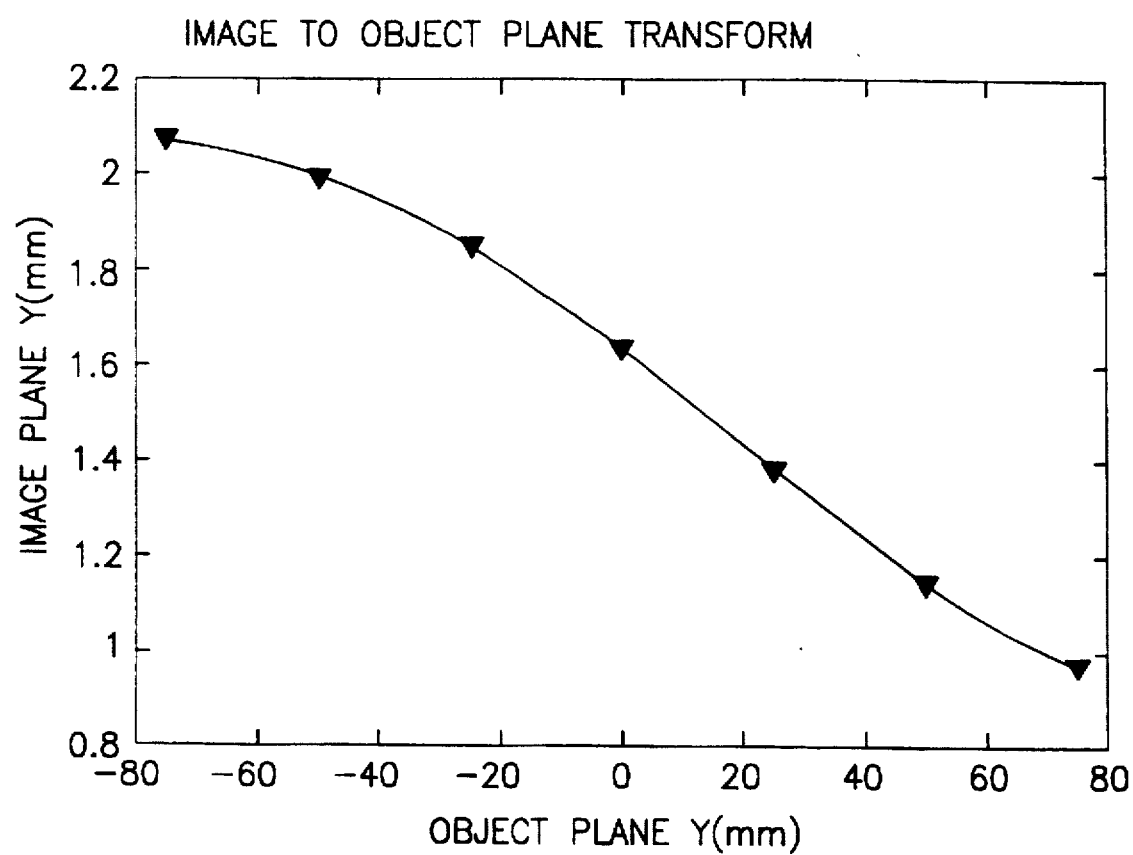
FIG. 5 shows the distortion correction curve used to go from FIG. 3 to FIG. 4.

FIG. 5 shows the image to object plane transform used to go from the image of FIG. 3 to the image of FIG. 4. FIG. 5 shows points along the image plane on the ordinate axis and points along the object plane on the abscissa axis. Code V can be used to generate a look-up table giving the correspondence between points on the image plane (FIG. 3) and points on the object plane (FIG. 4). The look-up table also removes the left-right reversal, as can be seen by the numbers 1, 3, and 5 in FIG. 4.

In some cases it may be desirable to suspend a spinner flowmeter below the video logging tool of the present invention. The weight of the spinner and the torsion caused by it might require strengthening the video logging tool. While the struts 80 of the embodiment shown in FIG. 2 could be increased in size, this would have the effect of increasing the obstruction of the side view.

Figure 6:
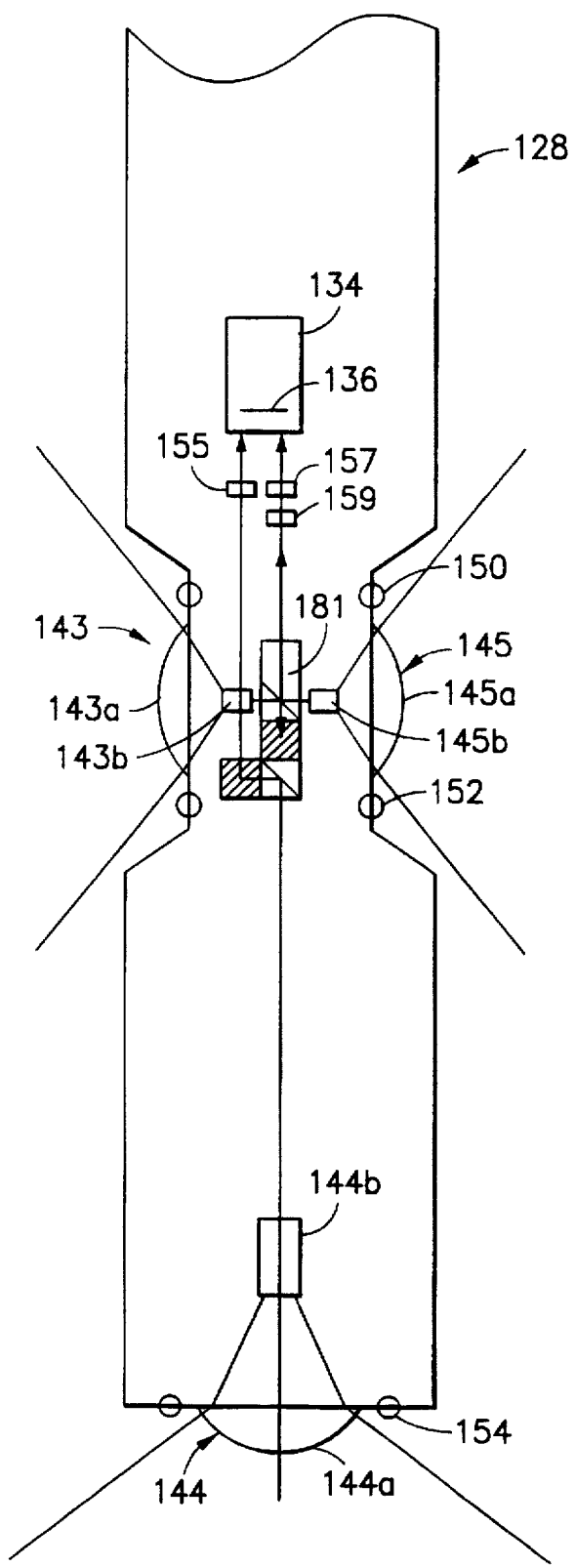
FIG. 6 is a schematic diagram of another embodiment of the invention.

FIG. 6 shows another embodiment of the invention which provides increased mechanical strength while nevertheless maintaining an acceptable circumferential side view. FIG. 6 shows the optical module 128 of the tool, comprising a CCD camera 134 having a CCD array 136 in its image plane. The tool comprises an end viewing optical system including a fish-eye lens 144 comprising an external lens group 144a and an internal lens group 144b both of which are made up of multiple elements. The tool also has a side viewing optical system comprising a left and a right fish-eye lens 143 and 145 respectively, comprising external lens groups 143a, 145a and internal lens groups 143b, 145b, all of which are made up of multiple elements. A plurality of LEDs 150 are disposed circumferentially around the optical module 128 above the fish-eye lenses 143 and 145, and a second plurality of LEDs 152 is likewise disposed below the fish-eye lenses. Another plurality of LEDs 154 are disposed in a ring around the end viewing lens 144. The LEDs 150 and 152 light the side view and the LEDs 154 light the end view. As in the embodiment of FIG. 2, the LEDs have a predominant wavelength of 880 nanometers in the near infrared.

In the embodiment of FIG. 2, the end and side view images are concentric. This allows much of the optical systems of the end and side views to be common, although the light rays from the end and side views travel through these common optical elements along different paths. In the embodiment of FIG. 6, the left and right side views must be separated from each other and from the end view. The three views are still imaged onto the same image plane constituted by the CCD array 136.

Figure 7:
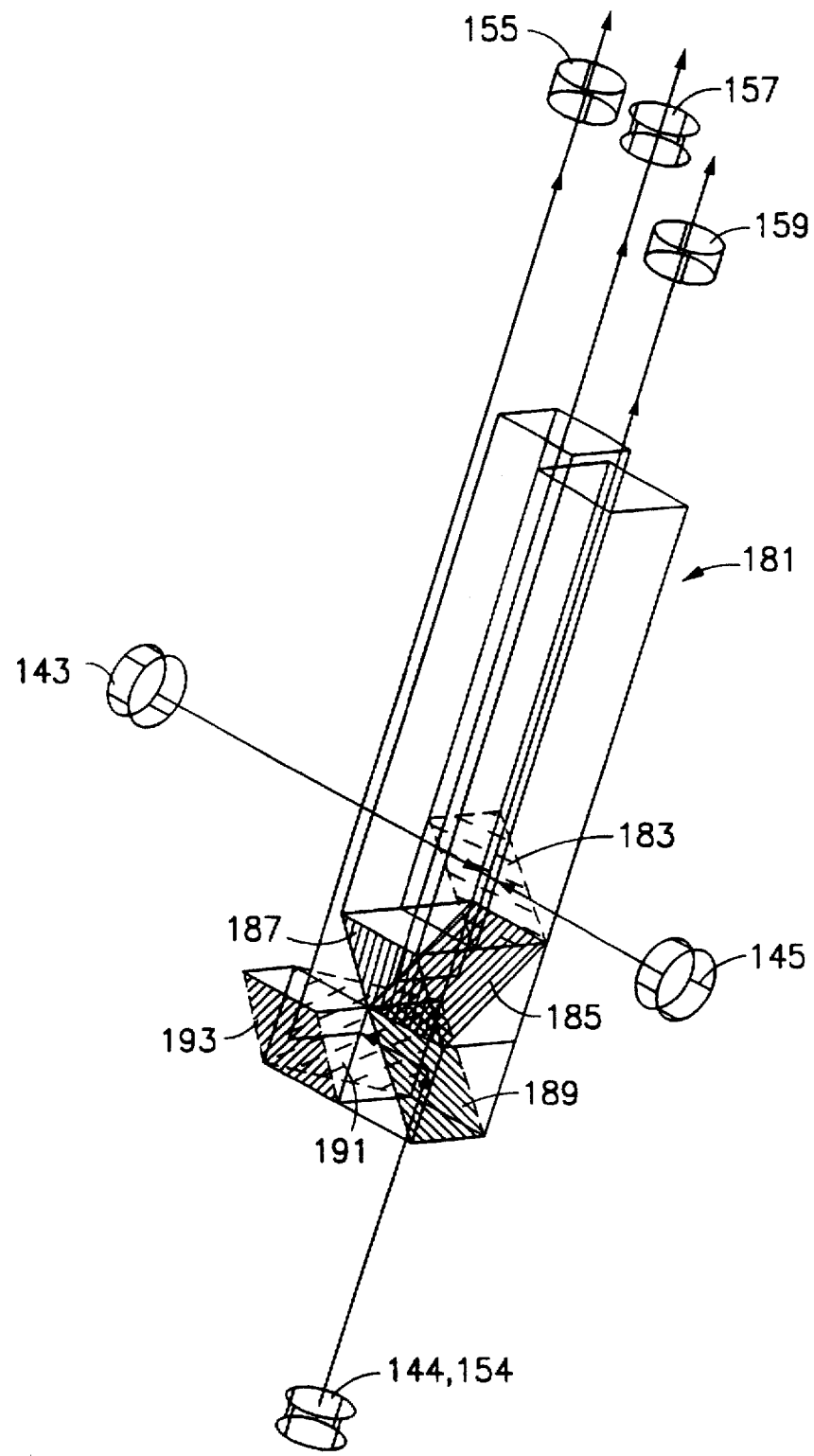
FIG. 7 is a view of the optical prism used in the embodiment of FIG. 6.

The left, right and end views are separated from each other laterally by a prism 181 shown in FIGS. 6 and 7. The left and right fish-eye lenses 143, 145 and the end viewing optical system 144, 154 each comprise objectives for the CCD camera 134. Unlike the embodiment of FIG. 2, in the embodiment of FIGS. 6 and 7, each view has its own camera lens for imaging the corresponding view in the plane of the CCD array 136. This is shown in FIG. 7, which also shows the prism 181 for separating the three views.

Figure 8:
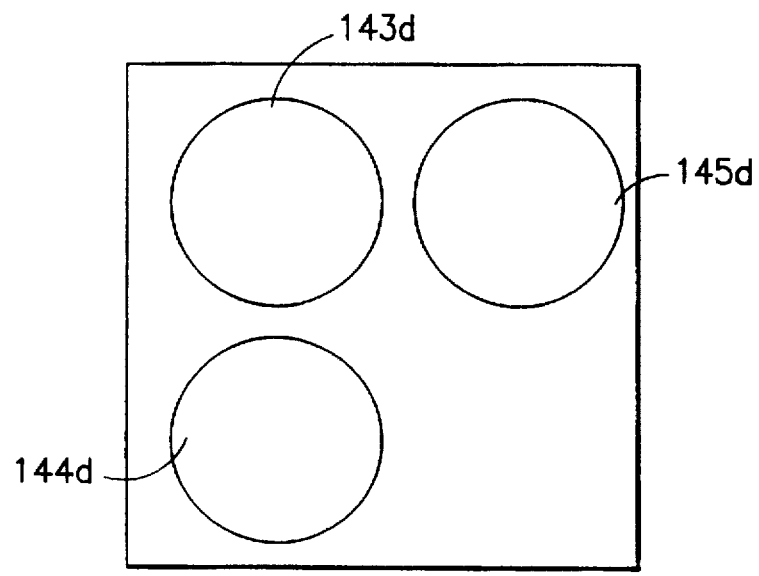
FIG. 8 shows the CCD array maps for the embodiment of FIG. 6.

The central ray path for each view will now be described briefly. The light rays from the right fish-eye lens 145 are reflected upwardly from the prism face 183 to a camera lens 159. Light rays from the left fish-eye lens 143 are reflected downwardly from the other side of the surface 183 to the surface 185 where they are reflected laterally to the surface 187 and upwardly to the camera lens 157. Light rays from the end viewing optics 144, 154 are reflected laterally at the prism surface 189, and again at the surface 191 and finally they are reflected upwardly at the surface 193 to reach the camera lens 155. All three views are imaged onto the CCD array 136 as shown in the array map of FIG. 8, in which the left and right view images are shown at 143d and 145d, and the end view image is shown at 144d.

Figure 9:
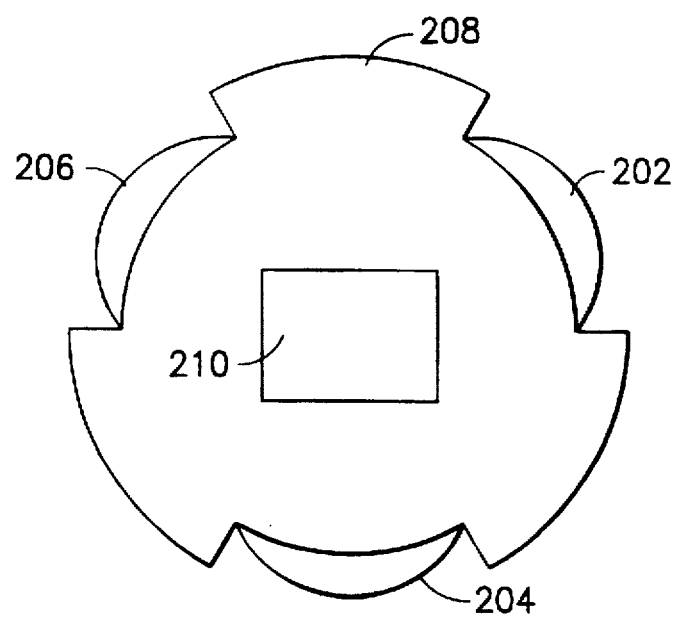
FIG. 9 is a schematic cross section of another embodiment of the invention.
Figure 10:
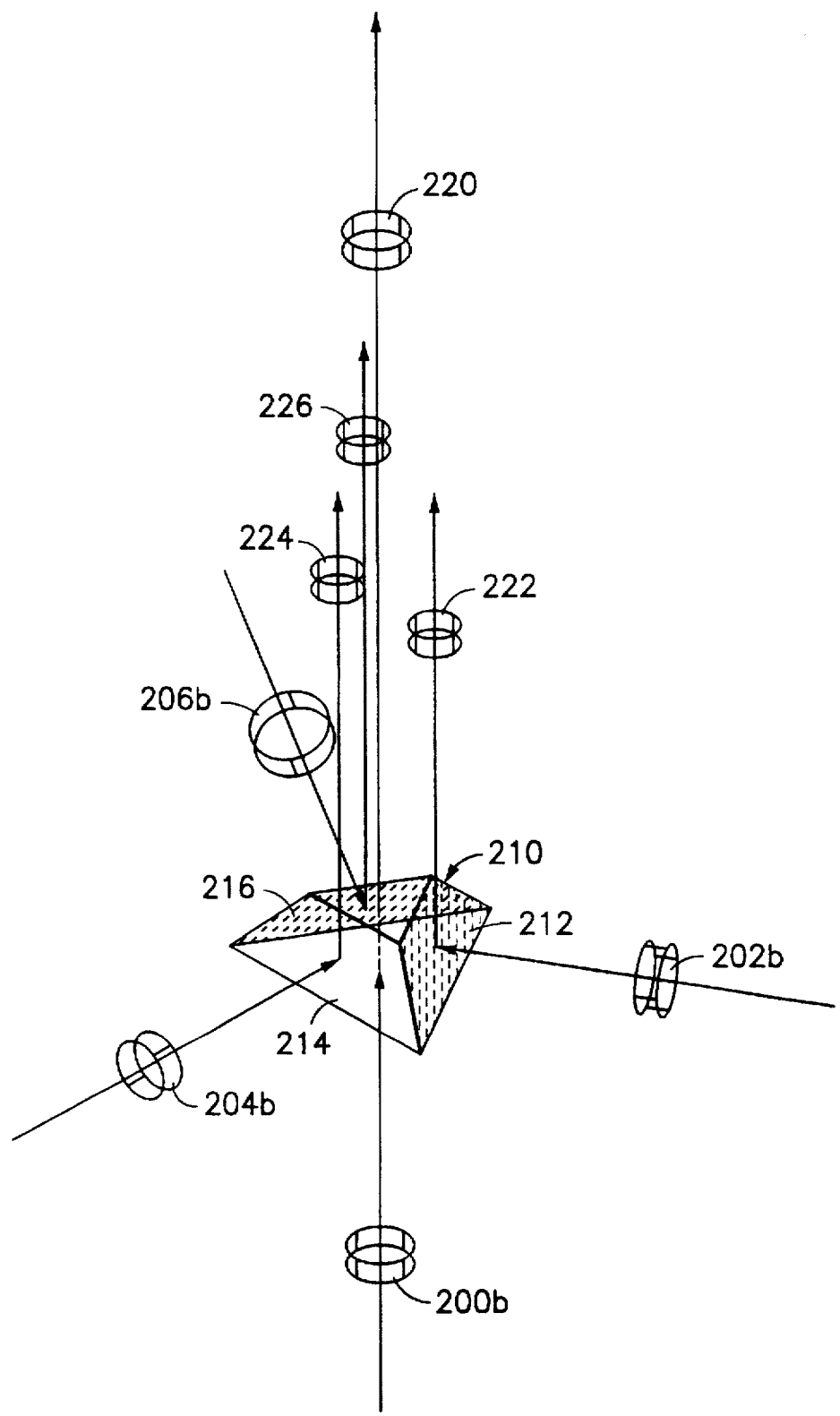
FIG. 10 is a view of the optical prism used in the embodiment of FIG. 9.

The embodiment of FIGS. 6 and 7 will provide somewhat less than 360 degree cicumferential viewing, depending on the design of the fish-eye lenses. Full 360 degree viewing can be achieved with three fish-eye lenses disposed at 120 degrees to each other, as shown in the embodiment of FIGS. 9 and 10. The three fish-eye lenses are designated 202, 204 and 206, and are mounted in a housing 208. A prism 210 is disposed in the middle of the housing to reflect the three side view images towards a camera (not shown).

The prism 210 is shown in more detail in FIG. 10. It has the shape of a truncated triangular pyramid with three side faces 212, 214, 216 angled at 45° to reflect the side view images from fish-eye lens internel lens group 202b, 204b, 206b to three separate camera lenses 222, 224, 226 which focus the images onto a CCD array in the image plane of the camera. This embodiment also has an end viewing fish-eye lens of which the internal lens group is shown at 200b. The end view image passes through the prism 210 from bottom to top, and is focused on the CCD array by a fourth camera lens 220.

With this arrangement the three side images are positioned on the CCD array at the three comers of a triangle, with the end image in the center of the triangle. A more efficient use of the area of the CCD array would be to position the four images at the corners of a rectangle, and this can be accomplished by using turning prisms or fiber optics.

In both fish-eye embodiments of FIGS. 6 and 9, distortion can again be removed with the computer software Code V. Although Code V has been used in the present application, other comercially available software programs can be used.

The video images obtained by the CCD cameras 34 (FIG. 2) or 134 (FIG. 6) can be sent to the surface at the rate of about 30 frames per second over fiberoptic cable. However we prefer to use standard copper wireline cable for the sake of compatibility with other downhole tools and surface equipment. Such standard wireline cable does not have the necessary bandwidth, so the video signal is compressed in the data processing block 58 for example of FIG. 1. Several video compression techniques are known. One such technique is JPEG which is often used in video compression for computer displays. We prefer wavelet compression techniques such as described in "Embedded Image Coding Using Zerotrees of Wavelet Coefficients" by Jerome M. Shapiro—IEEE Transactions on Signal Processing, Vol. 41, No. 12, Dec. 1993, or "A New, Fast, and Efficient Image Codec Based on Set Partitioning in Hierarchical Trees" by Amir Said and William A. Pearlman, which appeared in IEEE Transactions on Circuits and Systems for Video Technology , Vol. 6, No. 3, June 1966. Other compression techniques could also be used. Video compression techniques degrade the signal somewhat, and it may also be necessary to transmit a signal of reduced resolution or lower frame rate. Such compromises are acceptable in the context of production well logging.

We claim:

1. A video inspection tool for inspecting the inside of a borehole or pipeline, comprising:
   a housing having an end and a side and being adapted to moved through the borehole or pipeline
   a camera mounted in the housing;
   end lighting means adapted to light an outer end zone;
   side lighting means adapted to light an outer side zone;
   an end window for viewing outwardly into the end zone;
   a side window for viewing outwardly into the side zone;
   an end optical system for transmitting light from the end zone through the end window and to the camera; and
   a side optical system for transmitting light from the side zone through the side window and to the camera.

2. A tool according to claim 1, wherein the camera has an image plane common to end and side views.

3. A tool according to claim 2 wherein the camera comprises a CCD camera having a CCD in its image plane.

4. A tool according to claim 1, wherein the side window comprises a transparent block.

5. A tool according to claim 4, wherein the side optical system comprises a concave surface in said block, said concave surface facing the end of the housing and being coated with a mirror.

6. A tool according to claim 5, wherein the end optical system comprises an aperture in the mirror together with said block.

7. A tool according to claim 6, wherein the end and side optical systems comprise at least some, optical elements, said common, optical elements including said block and a camera lens group disposed in front of the camera.

8. A tool according to claim 1, wherein the end and side optical systems comprise at least some common optical elements.

9. A tool according to claim 8, wherein the common optical elements comprise a camera lens group disposed in front of the camera, said lens group comprising, in the direction of propagation of light toward the camera, a bi-concave lens, a plano-convex lens and a doublet.

10. A tool according to claim 4, wherein the end optical system comprises, in the direction of propagation of light toward the camera, a first concave convex meniscus lens and a second concave convex meniscus lens, and said block.

11. A tool according to claim 10, wherein the first concave convex meniscus lens comprises the end window and is pressure resistant.

12. A tool according to claim 1, wherein the end lighting means comprises a plurality of light emitting diodes.

13. A tool according to claim 12, wherein said light emitting diodes are disposed around the end window and directed onto the side zone.

14. A tool according to claim 1, wherein the side lighting means comprises a plurality of light emitting diodes.

15. A tool according to claim 14, wherein said light emitting diodes are disposed adjacent to the side window and directed into the side zone.

16. A tool according to claim 4, wherein the side lighting means comprises a plurality of LEDs disposed circumferentially around the housing above the block and a plurality of LEDs disposed circumferentially around the housing below the block.

17. A tool according to claim 12, wherein the LEDs emit light in the near infra-red.

18. A tool according to claim 1, wherein the endlighting means and the side lighting means each comprise a plurality of LEDs, means being provided for modulating said LEDs on and off so as to conserve power.

19. A tool according to claim 18, comprising means for modulating the camera on and off in synchronism with the LEDs.

20. A tool according to claim 1, wherein at least one of the windows comprises sapphire.

21. A tool according to claim 1, wherein at least one of the windows comprises a sapphire coating on its outer surface.

22. A tool according to claim 1, comprising data compression means for compressing the images taken by the camera, and telemetering means for transmitting the compressed images to the surface.

23. A tool according to claim 22, wherein said telemetering means comprises an electrical cable having metal conductors.

24. A tool according to claim 5, wherein the mirror distorts the side view image, means being provided for remapping the distorted image into rectilinear co-ordinates.

25. A video inspection or logging tool, comprising a housing;

a camera mounted in the housing and comprising an image plane;

an optical block mounted in the housing said optical block having a concave surface coated with a mirror for reflecting light from the side of the housing towards the camera;

a camera lens group disposed between the block and the camera for focusing light reflected from the mirror onto the image plane of the camera; and side lighting means disposed in the housing for lighting a side zone outside the optical block.

26. A tool according to claim 25, wherein said lighting means comprises a plurality of LEDs emitting in the infrared.

27. A tool according to claim 1, wherein said side optical system comprises a plurality of fish-eye lenses for transmitting side images into the housing, and prism means inside the housing for directing the images from each fish-eye lens separately to the camera.

28. A tool according to claim 27, wherein said optical system comprises a fish-eye lens for transmitting an end image into the housing, said prism directing the end image separately to the camera.

* * * * *